United States Patent
Windhab et al.

(10) Patent No.: US 11,666,668 B2
(45) Date of Patent: Jun. 6, 2023

(54) MASKING AND SUBSEQUENTLY VISUALISING ESR SIGNALS USING THE COMBINATION OF TWO MATERIALS

(71) Applicant: Evonik Operations GmbH, Essen (DE)

(72) Inventors: Norbert Windhab, Hofheim (DE); Andreas Karau, Gelnhausen (DE); Peter Hölig, Waechtersbach (DE); Benedikt Hartwig, Darmstadt (DE); Julia Lyubina, Hanau (DE)

(73) Assignee: Evonik Operations GmbH, Essen (DE)

( * ) Notice: Subject to any disclaimer, the term of this patent is extended or adjusted under 35 U.S.C. 154(b) by 260 days.

(21) Appl. No.: 15/733,173

(22) PCT Filed: Nov. 23, 2018

(86) PCT No.: PCT/EP2018/082302
§ 371 (c)(1),
(2) Date: Jun. 3, 2020

(87) PCT Pub. No.: WO2019/110321
PCT Pub. Date: Jun. 13, 2019

(65) Prior Publication Data
US 2021/0164927 A1    Jun. 3, 2021

(30) Foreign Application Priority Data
Dec. 4, 2017   (EP) .................................. 17205099

(51) Int. Cl.
*A61K 49/18*      (2006.01)
*G01N 24/10*    (2006.01)
*G01R 33/60*    (2006.01)
*A61B 5/055*    (2006.01)
*A61B 5/00*     (2006.01)

(52) U.S. Cl.
CPC .......... *A61K 49/1827* (2013.01); *A61B 5/055* (2013.01); *A61B 5/4866* (2013.01); *G01N 24/10* (2013.01); *G01R 33/60* (2013.01)

(58) Field of Classification Search
None
See application file for complete search history.

(56) References Cited

U.S. PATENT DOCUMENTS

| | | | |
|---|---|---|---|
| 2008/0204855 A1* | 8/2008 | Yamamoto ............... | G02F 1/167 359/296 |
| 2015/0008914 A1 | 1/2015 | Hartwig et al. | |
| 2016/0135759 A1* | 5/2016 | Hartwig ................... | A61J 3/007 600/409 |

FOREIGN PATENT DOCUMENTS

| | | |
|---|---|---|
| JP | 2005-189219 | 7/2005 |
| WO | 2011/026808 | 3/2011 |

(Continued)

OTHER PUBLICATIONS

Machine English Translation of JP 2005189219A to Ri et al. (Year: 2005).*

(Continued)

*Primary Examiner* — Douglas X Rodriguez
(74) *Attorney, Agent, or Firm* — Grüneberg and Myers, PLLC (57) ABSTRACT

A body has multiple phases, which have different electron spin resonance spectra that do not result from the simple combination of the ESR spectra of each individual phase.

14 Claims, 4 Drawing Sheets

ESR spectra of ultramarine at 100 K and room temperature.

(56) References Cited

FOREIGN PATENT DOCUMENTS

WO  2013/091901    6/2013
WO  2014/202404    12/2014

OTHER PUBLICATIONS

Alenkina et al., Spechtrochimica Acta. Part A: Molecular and Biomolecular Spectroscopy, 2017,130, 24-36.
Tshabalala et al., Journal of Colloid and Interface Science, 2017, 304, 371-386.
European Search Report dated Jun. 1, 2018 in European Application No. 17205099.9.
International Search Report dated Mar. 4, 2019 in PCT/EP2018/082302.
Written Opinion dated Mar. 4, 2019 in PCT/EP2018/082302.
Berger et al., Journal of Magnetism and Magnetic Materials; 2001, 234: 535-544.
Brueckner, Angelika, Chem. Ing. Tech; 2014, 86 (11): 1871-1882, with English Abstract.
Brueckner, Angelika, Catalysis Reviews; 2003, 45 (1): 97-150.
Brueckner, Angelika, Topics in Catalysis; 2006, 38 (1-3): 133-139.
Dorfman, Ya.G, Experimental and Theoretical Physics Journal; 1965, 48 (Issue 2): 1-4.
Dyrek et al., Appl. Magn. Reason; 1996, 10: 319-338.
Heinrich et al., Advances in Physics; 1993, 42 (5): 523-639.
Salado et al., Journal of Non-Crystalline Solids; 2008, 354: 5207-5209.
Sharma et al., Journal of Applied Physics; 1977, 48: 4298-4302.
Vallejo-Fernandez et al., J. Phys. D: Appl. Phys; 2013, 46, 312001: 6 pages.

\* cited by examiner

Fig. 1a. ESR spectra of powder mixtures of UB and MAG in various weight ratios, recorded at room temperature.

Fig. 1b. Second derivatives of the ESR spectra with respect to $H_{appl}$.

Fig. 2. ESR spectra of thin films containing $Fe_3O_4$, ultramarine blue, MAG and UB in layers.

Fig. 3. ESR spectra: a) ultramarine blue (UB), b) phen(CuCl$_2$), c) UB and phen(CuCl$_2$) mixed in a weight ratio of 1:1, a) + b) direct sum of a) and b).

Fig. 4. ESR spectra of magnetite at various temperatures.

Fig. 5. ESR spectra of ultramarine at 100 K and room temperature.

Fig. 6. ESR spectra of ultramarine and magnetite as tablet (a) and suspended tablet (b).

MASKING AND SUBSEQUENTLY VISUALISING ESR SIGNALS USING THE COMBINATION OF TWO MATERIALS

TITLE OF THE INVENTION

CROSS-REFERENCE TO RELATED APPLICATIONS

This application is a National Stage entry under § 371 of International Application No. PCT/EP2018/082302, filed on Nov. 23, 2018, and which claims the benefit of European Application No. 17205099.9, filed on Dec. 4, 2017, the content of each of which is hereby incorporated by reference in its entirety.

BACKGROUND OF THE INVENTION

Field of the Invention

The invention relates to a body having multiple phases that have different electron spin resonance spectra.

Discussion of the Background

Systems with itinerant magnetism are known in great detail in the prior art, where band electrons show spontaneous magnetic order, and they are well distinguished from those systems wherein the magnetic order is caused by localized electron spins. The latter are important in chemically complexed atoms, especially almost all coloured minerals, often as technical fillers and pigments or rare earths. Other important paramagnetic centres are insulators, such as synthetic and natural polymers and organic dyes, such as quinoids, anthocyanins and polyphenols.

But the magnetic moment of localized electron spins is also increasingly affected by spin-orbit coupling effects in main and transition groups with increasing atomic number of the chemical element which is the atomic trunk corresponding to the localized electron spin. The material scientist is thus also aware of micro- and macroscopic spin-lattice systems up to and including metallic conductor bodies.

If the abovementioned systems, viz. ionic-atomic, chemical complexes, insulator radicals such as polymers, minerally inerted or naturally mineral, semimetallic or metallic systems, are irradiated with microwaves, what are accordingly obtained in the most general sense are different steady-state or dynamic electron spin resonance spectra, the term "electron spin resonance" being abbreviated to "ESR" in the context of the invention. In principle, only systems having unpaired electrons are amenable to ESR spectroscopy, for example free-radical systems, paramagnetic transition metals, strip magnets and semiconductors. The paper by Angelika Brückner in *Chem. Ing. Tech.* 2014, 86, 11, p. 1871-1882, sets out that, according to the system, the resonant electron spin may be subject to complex interactions, for example between electron spin and nuclear spin, and/or is influenced by the three-dimensional symmetry. In measurement on systems composed of multiple superposed components, this causes complex ESR spectra that are often not easy to interpret. Although this demonstrates the high potential of the spectroscopic method for the study of unpaired electron systems, it can be seen at the same time that a combination of different systems cannot easily be assigned to a linear or easily calculated combination of ESR spectra.

If the problem of following a given substance on its path through the human or animal organism is addressed, the challenge to be reckoned with is that of having to detect the position, the identity and the change in the ESR spectrum with time very accurately in order thus to be able to draw conclusions as to the physical and/or chemical transformation of the aggregate or of the substance, for example during its dissolution in the digestion process or in other processes in its metabolization.

Dorfman, *J. Exp. Theor. Phys.* 48 (1965), 715, assesses how macroscopic magnetic observables in such systems depend fundamentally on the grain size. Overall, in materials of relevance here, especially the medical-technical formulations, the behaviour of spin system, the "probe" of the overall aggregate that gives the moment, and legalistic-regulatory employability can thus be difficult to predict.

The intensity of the ESR signal, equivalent to the integral of the absorption signal, is directly proportional to the spontaneous magnetization $M_s$ of the sample, as set out in the paper by B. Heinrich and J. F. Cochran in *Advances in Physics* 42 (1993), 523. The line width of the ESR signal follows a dependence in the form of $$\Delta H \sim K_1/M_s$$

where $K_1$ is the magnetocrystalline anisotropy constant; cf. Ya. G. Dorfman, *J. Exp. Theor. Phys.* 48 (1965), 715. Magnetic shape anisotropy also has a significant effect on the shape and position of the ESR signal. Since the magnetocrystalline constants of anisotropy of the known ferro- or ferrimagnetic materials are in the region of 103-106 $J/m^3$, accordingly, an ESR line width $$\Delta H \sim (10^2 \ldots 10^4) \text{ Oe}$$

is observed. V. K. Sharma and F. Waldner in *J. Appl. Phys.* 48 (1977), 4298, observed the line width $\Delta H$ in ferrimagnetic $Fe_3O_4$ powder of ~1000 Oe at room temperature. It should be noted that the magnetocrystalline constant of anisotropy of magnetite is about $3*10^4$ $J/m^3$.

It is also known that, in particles at or below a critical size, thermal fluctuations are dominant over magnetocrystalline anisotropy above a critical temperature, also called blocking temperature, and hence such particles show superparamagnetic behaviour. Below the blocking temperature, by contrast, the particles have ferro- or ferrimagnetic behaviour. The critical size of the particles is determined by magnetocrystalline anisotropy. In magnetite, the critical particle size is about 14 nm; cf. G. Vallejo-Fernandez et al., *J. Phys. D: Appl. Phys.* 46 (2013), 312001. Magnetite nanoparticles having particle sizes at or below 14 nm can have relatively narrow ESR lines that are characteristic of paramagnetic and superparamagnetic particles, discussed in the paper by J. Salado et al., *J. Non-Crystalline Solids* 354 (2008), 5207, and in R. Berger, *J. Magn. Magn. Mater.* 234 (2001), 535.

A particular form of such measurements is the detection of paramagnetic influences on imaging nuclear spin tomography, but their measurement is based on much weaker nuclear spin interactions.

SUMMARY OF THE INVENTION

The inventors have completely surprisingly hit on a further, entirely different correlation.

While an ESR spectrum has been regarded as being typical of the substance being irradiated at the present state of knowledge, the problem to be solved is thus that of how systematically controlled and intended conversion processes on the substance, especially by combinations of various systems used successfully here, for instance in the form of mixtures, compounds or generally compositions composed of various macroscopic or microscopic phases, afford characteristic ESR spectra for the respective composition.

Compositions composed of at least two materials have been found, in which at least one material outside the composition in its pure form would give characteristic ESR spectrum. But in the composition with at least one further material, precisely that ESR spectrum is surprisingly significantly attenuated or has completely disappeared.

DETAILED DESCRIPTION OF THE INVENTION

The subject of the invention is accordingly a body that has multiple phases and is taken up by the human or animal organism or is within the organism, which is characterized in that the body has at least two phases with a different electron spin resonance spectrum. The subject here has the advantage of being in a non-physiologically or controversially toxicologically limited in terms of its vital functions by radiation or toxicity of the material.

At least one of the phases advantageously has itinerant or localized magnetism. ESR spectra of rare earths are found to be less well suppressed, and, according to the combination, the body according to the invention shows attenuation of the ESR spectrum or superimposition of different ESR spectra.

It may be advantageous when at least one phase of the body according to the invention has purely paramagnetic centres, preferably S radicals, preferably selected from ultramarine. It may be particularly advantageous, rather than ultramarine, to select superparamagnetic particles, preferably comprising or consisting of magnetite or maghemite or pyrites or non-containing compounds such as amethyst. In the case of such particles, a similar ESR signal is found.

Preferably, at least one phase of the body according to the invention has at least a collectively ordering state that may be ferro-, ferri- and/or antiferromagnetic. More preferably, this phase includes iron-oxygen compounds. Most preferably, at least one phase is magnetite or a phase composed of the Fe—O system. The phases mentioned are especially substances that are harmless to the human or animal organism. In addition, such selected phases may be pronounced in the form of a tablet formulation. What are surprising are the orders of magnitude of the effect that attenuates or suppresses the ESR spectrum.

The phases can additionally be reworked in particle dispersions. It is again surprising that it is thus possible in a simple manner to provide a pharmaceutical formulation since specifically magnetite or a material having Fe—O phases is of very good compatibility with respect to the human organism and even in human medicine would be extremely safe to use. The body according to the invention could thus likewise be used reliably in the gastrointestinal region because the body does not include any highly toxic substances or harmful free radicals.

Therefore, the invention likewise provides for use of the body according to the invention, wherein the ESR spectra are stored in a data storage device, and the data stored are preferably transmitted to a receiving device on receipt of a demand signal. Thus, use in a data management network is also advantageous.

A particularly advantageous use is in fingerprint spectroscopy, in copyright protection, and/or in nutrition.

In any spectroscopy, the better the signal-to-noise ratio of the system in question, the better the measurement results achieved, where the system in this case is the organism in question with the body according to the invention and the instrumentation for detection of the ESR spectrum. Human and animal organisms show by far predominantly diamagnetic behaviour in magnetic fields, and diamagnetic background barely disrupts even the much more sensitive nuclear spin tomography. Thus, when the body according to the invention is used, only very low magnetic field strengths are required for the measurement of the ESR spectra.

In addition, it may be advantageous that, in the body according to the invention, at least one phase is encased by at least one further phase. More preferably, one phase as a thin film encases a further phase.

Preferably, the thickness of the film and the phases may be selected such that the ESR spectrum of the inner, encased phase is fully concealed by the ESR spectrum of the outer, encasing phase.

If the passage of the body according to the invention through the human or animal organism is associated with the breakdown of the body, the ESR signal of the encased phase appears ever more strongly in a time-dependent manner with the breakdown of the encasing phase. This simple time dependence is a further advantageous property of the body.

If magnetite particles are selected in at least one phase of the body, the inventors are of the view, without being tied to a particular theory, that the ESR spectrum could be caused not just by intrinsic magnetic properties but also by dipole interactions between magnetite particles. The interactions are preferably influenced by the shape of the particles, for example sphere, needle, cube, and generally by the spatial distribution of the magnetite, for example film. These forms show different demagnetizing fields.

The more ferri- or ferromagnetic components the body according to the invention possesses, the more strongly the ESR signal is attenuated. In this context, absorption of the microwaves emitted in spectroscopy is suspected.

Also conceivable are bodies in which a ferromagnetic phase and a free-radical phase, for example an ultramarine phase, are present in spatial separation, preferably in the form of spatially separated agglomerates. This corresponds to a distinct ESR spectrum. If the body is then broken down, there is temporary mixing of the two phases, and, given a suitable ratio of one to the other phase, the ESR spectrum of one phase, preferably that of ultramarine, temporarily disappears entirely. Thus, the breakdown of the body in the organism can be assigned specifically to the breakdown process.

It may also be advantageous when the body according to the invention has at least three phases, where one phase is preferably paramagnetic, preferably selected from (phen)$CuCl_2$.

In this case, the ESR line shape is more complex, and time-resolved behaviour is obtained in the breakdown of the mixture of the phases, for example on breakdown of the body during the metabolic process in the organism, which is demonstrated by a time dependence of the ESR spectrum. Progressive breakdown can be documented.

Accordingly, preferably magnetic, paramagnetic and free-radical phases may be combined. If a body of such a composition is broken down in the organism, with the breakdown-related disappearance of the magnetic phase or the detachment thereof from the body, another, "final" ESR line shape appears, which is distinctly different from the ESR line shape of the undecomposed body according to the invention.

Such breakdown processes are advantageous in the case of non-therapeutic procedures, for example within the scope of personal, non-medically motivated questions of nutrition or nutrition habits.

However, the breakdown processes are also the target of medical implants, for example, in the functional coatings thereof and particularly oral administration forms of nutraceutical, dietetic or therapeutic formulations, for example capsules, tablets, films and granules and multiparticulate administration forms in food technology and, independently of that, medicament technologies. They can be designed very specifically via the choice of excipients used, for example of capsule shells, particle coatings and the medical technology materials used, and hence controlled via the formulation process. Preference is given here to using solubility, more preferably pH- and time-dependent solubility of such auxiliaries and excipients. In the case of medical-technical implants, it is particularly hydrolysis that leads to the desired absorption of matrices and coatings. Examples include the approved materials and polymers Eudragit® methacrylates and Resomer® polyesters, modified starches such as HMPC, HMPC-AS or polylactites and co-glycolites or co-caprolactone for surgical material, and absorbable medical technology coatings or implants. It is possible here for such insulator polymers, especially medical technology polymers, themselves to bear paramagnetic centres, as arise, for example, in irradiating sterilization by means of an electron beam or γ radiation. It is thus also preferable that the body according to the invention has at least one phase having at least one medical technology polymer having a paramagnetic centre, preferably isolated free radicals.

It is possible for the appearance of the final ESR line shape to be regarded as a fingerprint of the body during the breakdown in the organism. This is elucidated in detail in Example 2 and FIG. 3.

Since mixed phases are thus distinguishable from clean phases, and the breakdown of at least one phase of the body according to the invention is detectable, it is also possible to detect dosages, meaning mixtures of differently constructed bodies, in the organism.

What is thus likewise provided by the invention is the use of the body according to the invention that has at least three phases for the monitoring of breakdown processes in the human or animal organism.

EXAMPLES

The invention is elucidated in detail hereinafter by examples.

In the context of the invention, the term "room temperature" is understood to mean an ambient temperature of 20° C.

EXAMPLE 1

Inventive Body Comprising Ultramarine Blue and Magnetite

Magnetite $Fe_3O_4$ powder, abbreviated to "MAG" in the context of the invention, trade name "Cathay pure Black B2310", available from Cathay Industries, and ultramarine blue powder, abbreviated to "UB" or "ultramarine", trade name: "Kremer Pigment, Product No. 45000", were mixed using a mortar with the aid of a pestle in the weight ratios of MAG:UB=1:30, 3:30 and 4:30.

ESR spectra of the mixture thus obtained were recorded in the X band (9.5 GHz) at room temperature and a microwave energy of 6.3 mW, at a modulation frequency of 100 kHz and an amplitude of up to 5 Gauss.

In addition, thin layers containing MAG were applied in each case to different adhesive strips, with additional dilution of the concentration of the MAG with methyl cellulose, or UB, where each of these components had been provided beforehand in the form of a suspension in ethanol.

ESR spectra of the layers thus obtained were recorded.

In order to make sure that UB and MAG have entered into intimate contact, such that there was sufficiently large interaction with the $S_3$ radical, the ESR spectra were first recorded on separate thin layers. Subsequently, the ESR spectrum was recorded in each case on the mutually bonded adhesive strips.

Figure 1A:
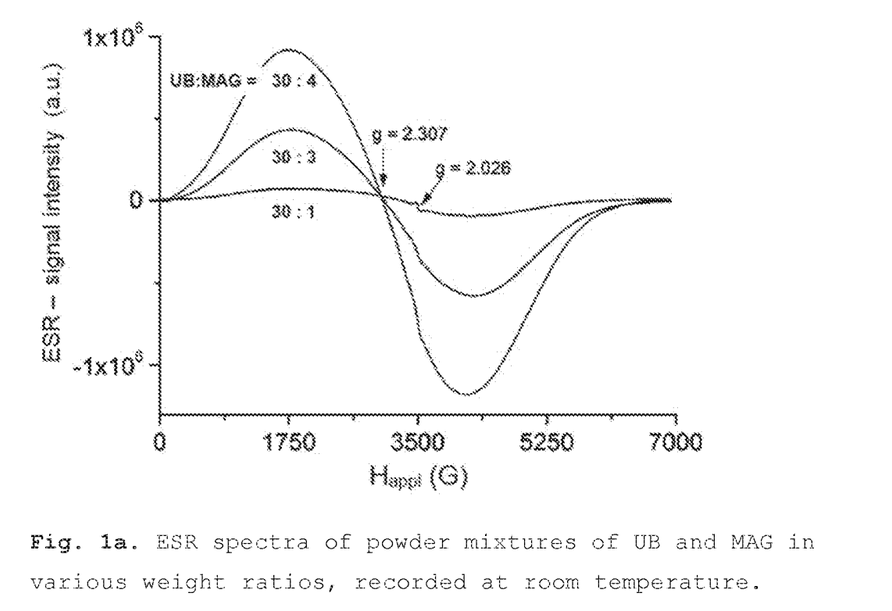
FIG. 1*a* shows ESR spectra of powder mixtures of UB and MAG in various weight ratios, recorded at room temperature.

FIG. 1a shows ESR spectra on various mixtures of MAG and UB.

At a weight-based mixing ratio of UB:MAG=30:1, the ESR signal of the $S_3$ radical at g=2.026 is still readily apparent. It can be concluded from this that not yet all $S_3$ radicals of the UB have entered into strong magnetic dipole interactions with MAG. But even in the case of an elevated MAG content, corresponding to a mixing ratio by weight of UB:MAG=30:3, a distinct, broad ESR signal was obtained at g=2.307 owing to the ferrimagnetic MAG particles. The signal of the $S_3$ radicals, by contrast, was barely still apparent owing to the strong magnetic interaction between MAG and $S_3$ radical. In the case of a proportion by weight of MAG increased to a ratio of UB:MAG=30:4, this effect was further enhanced.

Figure 1B:
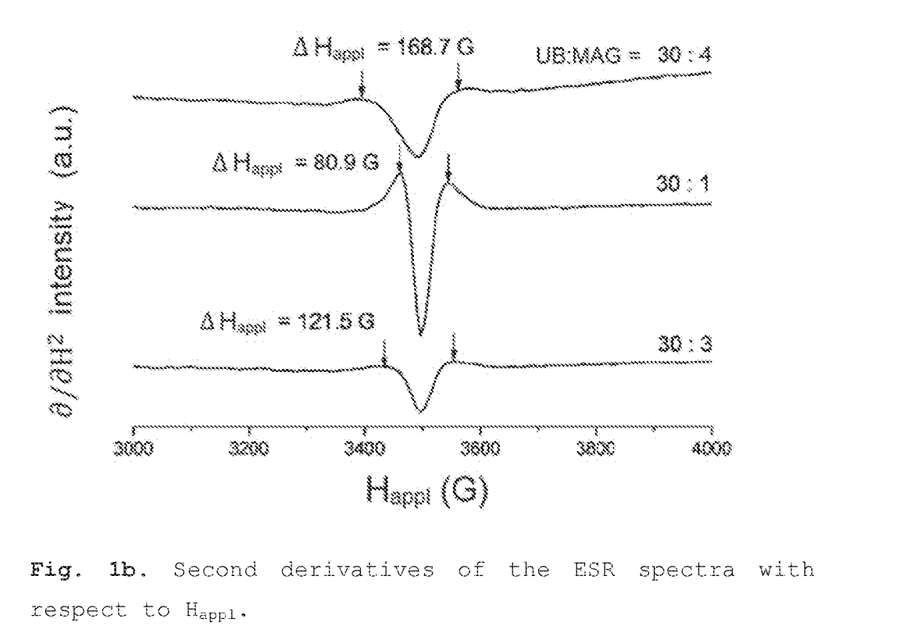
FIG. 1*b* shows second derivatives of the ESR spectra with respect to $H_{appl}$.

The second derivative of these line forms with respect to the external magnetic field $H_{appl}$ employed for the spectroscopy was shown by the diagram in FIG. 1b. The twice-differentiated line forms showed the radical signal even more clearly here, especially at the UB:MAG ratio=30:4.

The influence of the magnetic interactions between MAG and UB that rises with the MAG content was perceptible in the respective peak-to-peak distance in the second-derivative line form with respect to the magnetic field.

Figure 2:
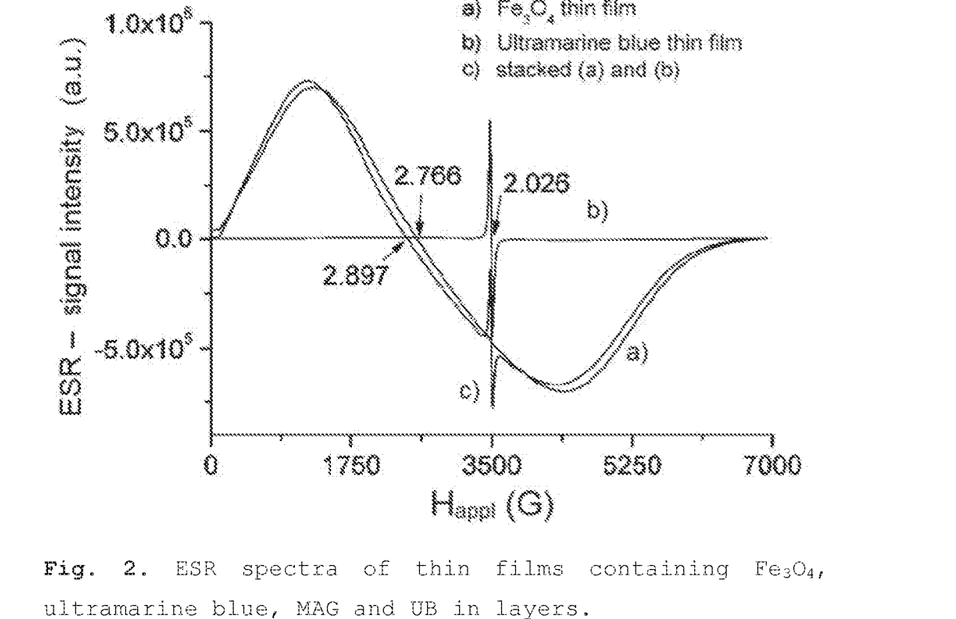
FIG. 2 shows ESR spectra of thin films containing $Fe_3O_4$, ultramarine blue, MAG and UB in layers.

FIG. 2 shows ESR spectra that were obtained on thin layers of UB and MAG on adhesive strips.

As expected, the ESR signals of the layers comprising MAG and comprising UB corresponded to the ESR signals of the pure MAG and UB components.

If, however, an intimate bond was provided by the sticking of the adhesive strips onto one another, different ESR signals were obtained.

The intensity of the ESR signal caused by the $S_3$ radical was found to be attenuated, whereas the ESR signal of the MAG barely lost any intensity but had undergone a slight shift from a value of g=2.766 to g=2.897.

It is assumed that this effect was attributable to the magnetic dipole interaction between MAG and UB, which probably means that even the mechanical contacting of the thin layers onto the adhesive strip simultaneously affected the ESR signal of the S₃ radical and the ferromagnetic ESR signal.

The ESR spectra just demonstrated show that, in mixtures of UB and MAG, a proportion of MAG of even about 10% by weight is sufficient to suppress the ESR signal of the radical below the detection limit. Even the contacting of thin layers containing both components attenuated this signal to about half the value.

If, by contrast, exclusively a paramagnetic component was mixed with UB, the S₃ radical ESR signal was obtained in virtually unchanged form, even when the proportion of the paramagnetic component was much higher than that of MAG.

Without being tied to a particular theory, the inventors suspect the cause of the shift in the ESR signal in FIG. 2 to lie in the magnetic state of the particles that causes self-demagnetization. The resulting internal field $H_{int}$ can be approximated by a simple relationship:

$$H_{int} = H_{appl} - N M,$$

where M is the magnetization, N is the demagnetization factor and $H_{appl}$ is the external magnetic field employed for the spectroscopy. The demagnetization depends on the geometry of the M-comprising particles or substance and the global form of the body that consists of such particles or substance. In the form of a layer, for example, that led to the spectrum in FIG. 2, a much stronger demagnetizing field is found when the outer magnetic field is applied perpendicularly to the layer surface than is brought about by spherical or cubic particles or bodies. N here can be assumed to be close to 1.

In the case of spherical or cubic particles or bodies that in particular are not in a layer arrangement, N can be set at ≈⅓. It is also suspected that the demagnetizing field causes the shift in the ESR spectra as a result of a change in magnetostatic interaction when the layers containing magnetite and ultramarine are stacked one on top of another than the abovementioned dipole interactions in the case that magnetite and ultramarine are mixed together.

EXAMPLE 2

Body Comprising phen(CuCl₂) and Ultramarine Blue

As Example 1, except that the mixture, rather than with MAG, was provided with paramagnetic dichloro(1,10-phenanthroline)Cu$^{II}$ (phen(CuCl₂)) complex and ultramarine blue in a weight ratio of 1:1.

While a considerable attenuation effect was observed in Example 1 because of the strong magnetic interaction between MAG and the S₃⁻ radical anion of ultramarine blue, this interaction was absent between the paramagnetic component with Cu$^{II}$ ions (d⁹, spin=½), namely the phen(CuCl₂) complex.

Figure 3:
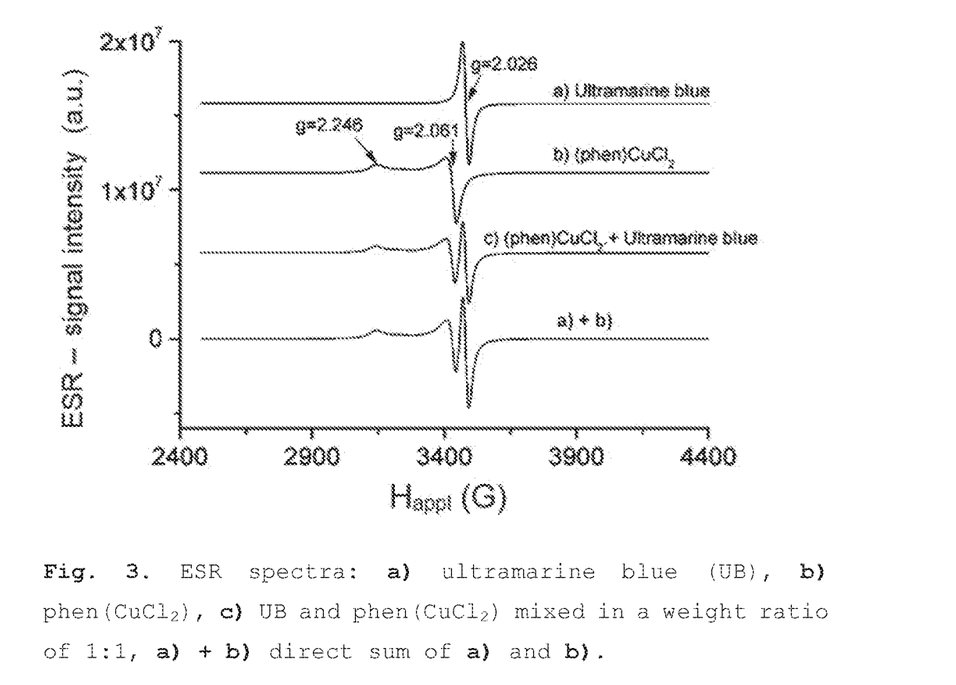
FIG. 3 shows the following ESR spectra: a) ultramarine blue (UB), b) phen($CuCl_2$), c) UB and phen($CuCl_2$) mixed in a weight ratio of 1:1, a) +b) direct sum of a) and b).

The ESR spectrum of the paramagnetic phen(CuCl₂) complex showed the typical signals of Cu$^{II}$ at g=2.246 and g=2.061, shown in FIG. 3, line shape b). The mixture with UB gave the ESR spectrum as a superimposition of Cu$^{II}$ and the S₃⁻ radical (FIG. 3, line shape c)). Line shape c) obviously corresponded in a very good approximation to the direct sum total of line shapes a) and b); see FIG. 3, line shape a)+b). This demonstrates a vanishing magnetic interaction between Cu$^{II}$ and S₃⁻ of ultramarine blue.

EXAMPLE 3

Inventive Body as Tablet Suspended in Water

Figure 6:
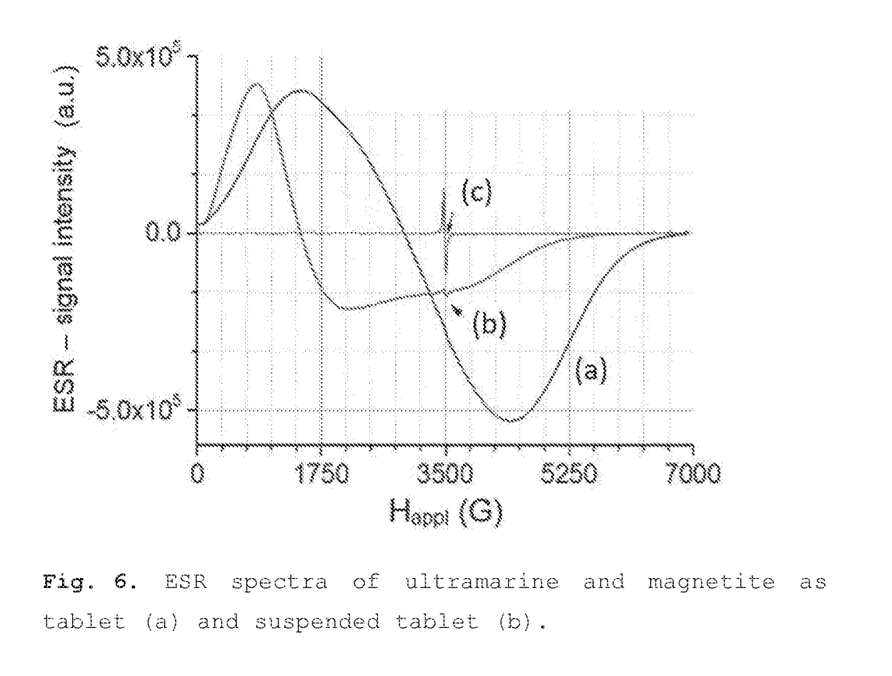
FIG. 6 shows ESR spectra of ultramarine and magnetite as tablet (a) and suspended tablet (b).

A mixture of 10 mg of Fe₃O₄, 10 mg of ultramarine blue and 130 mg of methyl cellulose was pressed to a tablet by subjecting the mixture to a pressure of 10 bar for 2 min. The tablet thus obtained was comminuted and suspended in water in a beaker. For the ESR measurements, samples of the suspension were introduced into a glass capillary after different times. Different ESR spectra were obtained as a function of time, which are shown in FIG. 6, specifically with line shape (a) the as yet unsuspended tablet and with line shape (b) the signal of the tablet after advanced suspension.

The apparent total intensity of the ESR signal demonstrates the altered content of suspended solids with time. The inventive monitoring of breakdown processes is thus also possible for simple dissolution of the body according to the invention. Line shape (c) in FIG. 6 shows the magnetite-free ESR signal for comparison.

Comparative Example

ESR Measurements on Pure Magnetite or Ultramarine

ESR spectra were recorded in the band at different temperatures on one solid sample each of magnetite, trade name "Cathey Pure Black B2310 (40969)", and one sample of ultramarine, trade name "Kremer Pigment (45000)".

Figure 4:
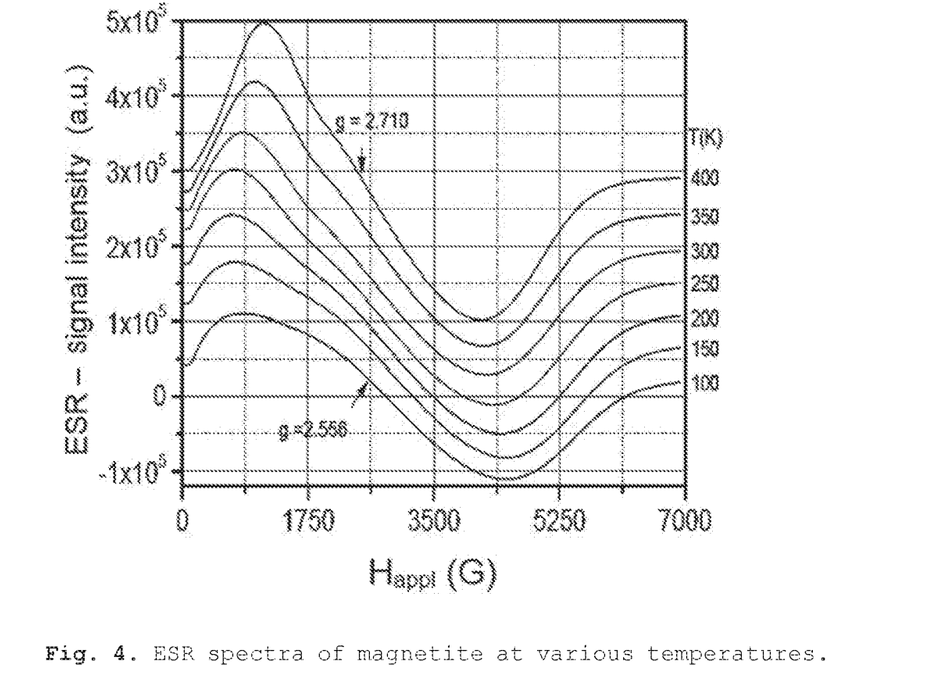
FIG. 4 shows ESR spectra of magnetite at various temperatures.

Pure magnetite showed the typical broad asymmetric singlet for ferromagnetic behaviour, the line shape of which changed reversibly with rising temperature, shown in FIG. 4. Such behaviour is probably attributable to the superimposition of ferromagnetic domains of different structure and/or orientation.

Figure 5:
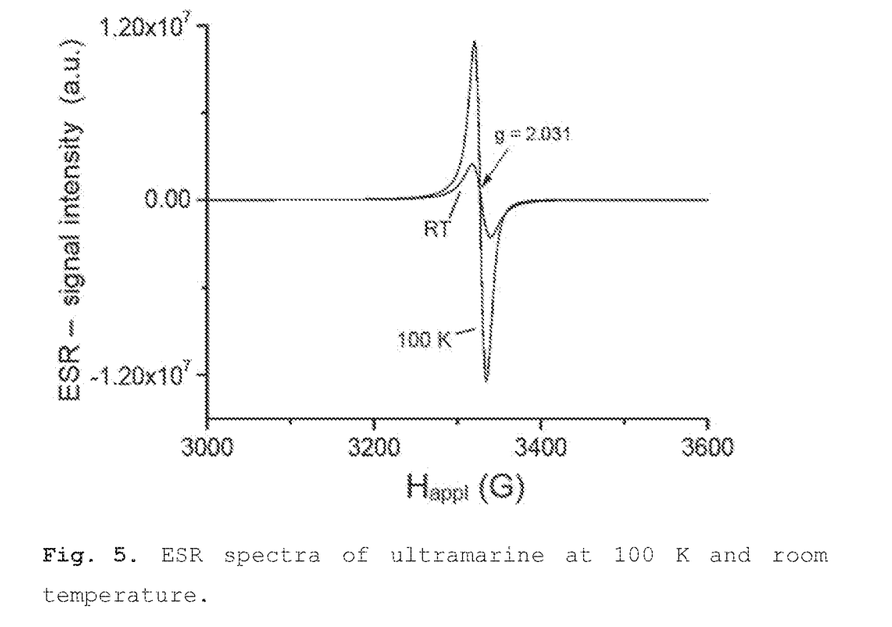
FIG. 5 shows ESR spectra of ultramarine at 100 K and room temperature.

The ESR spectrum of ultramarine contained a narrow isotropic signal that was attributable to the S₃ radical; see FIG. 5. Typical temperature behaviour was observed for purely paramagnetic centres, i.e. the intensity rose with falling temperature.

The invention claimed is:

1. A body having multiple phases, which is accommodated by a human or animal organism or is present within the organism, the body comprising:
    at least two phases having a different electron spin resonance (ESR) spectrum, at least one of the at least two phases of the body comprises a medical grade polymer having a paramagnetic center,
    wherein the body is selected from the group consisting of a medical implant or an oral dosage form for a nutraceutical, dietary, or therapeutic formulation,
    wherein at least one phase has S radicals and is ultramarine.

2. The body according to claim 1, wherein at least one phase has purely paramagnetic centers.

3. The body according to claim 1, wherein at least one phase has at least one collectively ordering state, selected from the group consisting of ferro-, ferri-, antiferromagnetic, and a combination thereof.

4. The body according to claim 3, wherein the at least one collectively ordering state is selected from the group consisting of iron-oxygen compounds.

5. The body according to claim 4, wherein the at least one collectively ordering state is magnetite or a material having Fe-O phases.

6. The body according to claim 1, wherein at least one phase is ensheathed by at least one further phase.

7. The body according to claim 1, wherein the at least two phases are mixed form.

8. The body according to claim 1, wherein the body has at least three phases.

9. The body according to claim 8, wherein the at least one phase of the at least three phases is $(phen)CuCl_2$.

10. A method, comprising:
   obtaining ESR spectra of the body according to claim 1, and
   storing the ESR spectra in a data storage unit.

11. The method according to claim 10, wherein the method is for a data management network.

12. The method according to claim 10, further comprising:
   transmitting the data stored to a receiving device on receipt of a demand signal.

13. A method, comprising:
   monitoring of breakdown processes in the human or animal organism with the body according to claim 1,
   wherein the body has at least three phases.

14. The body according to claim 1, wherein the medical grade polymer having the paramagnetic center has isolated radicals.

* * * * *